(12) United States Patent
Fabris Monterumici et al.

(10) Patent No.: US 8,002,833 B2
(45) Date of Patent: Aug. 23, 2011

(54) CONNECTABLE INTERBODY IMPLANT

(75) Inventors: Daniele A. Fabris Monterumici, Padua (IT); Rudolf Bertagnoli, Vienna (AT); Mingyan Liu, Bourg la Reine (FR); Loic Josse, Palaja (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 1670 days.

(21) Appl. No.: 10/505,969

(22) PCT Filed: Feb. 25, 2003

(86) PCT No.: PCT/IB03/00713

§ 371 (c)(1),
(2), (4) Date: Feb. 10, 2005

(87) PCT Pub. No.: WO03/071992

PCT Pub. Date: Sep. 4, 2003

(65) Prior Publication Data

US 2005/0119747 A1    Jun. 2, 2005

(30) Foreign Application Priority Data

Feb. 26, 2002 (FR) .................................. 02 02428

(51) Int. Cl.
*A61F 2/44* (2006.01)
(52) U.S. Cl. ...................... 623/17.14; 623/17.11
(58) Field of Classification Search .......... None
See application file for complete search history.

(56) References Cited

U.S. PATENT DOCUMENTS

| | | | | |
|---|---|---|---|---|
| 2,947,053 A * | 8/1960 | Sanderson | ........................ | 24/662 |
| 4,904,261 A * | 2/1990 | Dove et al. | ................. | 623/17.16 |
| 4,997,432 A | 3/1991 | Keller | | |
| 5,062,852 A * | 11/1991 | Dorr et al. | ................... | 623/20.33 |
| 5,397,364 A | 3/1995 | Kozak et al. | | |
| 5,554,194 A * | 9/1996 | Sanders | ..................... | 623/17.17 |
| 5,861,041 A | 1/1999 | Tienboon | | |
| 6,224,599 B1 | 5/2001 | Baynham et al. | | |
| 6,432,107 B1 | 8/2002 | Ferree | | |
| 2002/0029084 A1 | 3/2002 | Schenk et al. | | |

FOREIGN PATENT DOCUMENTS

| | | |
|---|---|---|
| DE | 43 23 595 C | 7/1994 |
| DE | 201 16 410 U | 11/2001 |
| EP | 1 043 002 A | 10/2000 |
| EP | 1 222 903 A | 7/2002 |
| WO | WO 99 60837 A | 12/1999 |
| WO | WO 00 22998 A | 4/2000 |
| WO | WO 00 25707 A | 5/2000 |
| WO | WO 00 67651 A | 11/2000 |
| WO | WO 01 28469 A | 4/2001 |
| WO | WO 01/28469 A2 * | 4/2001 |
| WO | WO 01 62166 A | 8/2001 |
| WO | WO 02 09606 A | 2/2002 |
| WO | WO 02 071986 A | 9/2002 |

* cited by examiner

*Primary Examiner* — Corrine M McDermott
*Assistant Examiner* — Christopher D Prone (57) ABSTRACT

An intersomatic implant (1a, 1b) maintains bone graft material in a receiving cavity formed in a disc in order to obtain intervertebral fusion. The implant (1a, 1b) includes of a plurality of parts provided with means for in situ connection of two consecutive parts. Instruments (33) are used to connect these implants (1a, 1b) and a tool assists in introducing these implants (1a, 1b) into the cavity formed in the disc.

25 Claims, 9 Drawing Sheets

CONNECTABLE INTERBODY IMPLANT

BACKGROUND

The present invention generally concerns the field of interbody implants with which it is possible to obtain fusion of two adjacent vertebrae when the disc separating them has been damaged, and more specifically, but not exclusively, it concerns the implants commonly referred to as "interbody cages" or "intersomatic cages" which are intended to receive a bone graft and to maintain the latter in place during the fusion, after partial excision of the damaged disc.

When a disc separating two vertebrae has degenerated and interbody fusion is necessary, this can be obtained by implanting interbody cages in cavities formed in the degenerated disc. The interbody cages are often fitted by the anterior route, in which case it is possible only to provide a single cage of this type, implanted in the central region of the disc. However, when the lumbar region is involved, an approach by the posterior route is possible on account of the fact that the nervous system there is less dense than in the other regions of the spine. There is therefore less risk of damaging the nervous system there during the surgical intervention. Nevertheless, the presence of the medullary canal in practice requires the use of two small sized interbody implants that are symmetrically arranged relative to the axis of the spine. These bilateral implants are separate components that are not connected to one another. There is therefore a risk of relative displacement or expulsion of the implants, especially since an implant of small size is less stable, in particular rotationally less stable, than an implant of larger size.

SUMMARY

One object of the present invention is to provide a unique interbody implant for spinal fusion and corresponding method to facilitate implantation of the implant.

In the case of intervertebral fusion by a posterior approach performed in the lumbar region, one object of the invention is to provide surgeons with the possibility of using interbody implants having a high degree of stability, while at the same time guaranteeing, as in current practice, a high level of safety during fitting of the implants.

To this end, the invention relates to an interbody implant for inserting and maintaining a bone graft in place in a receiving seat formed in a disc with a view to obtaining intervertebral fusion, characterized in that it consists of a plurality of parts provided with means for in situ connection of two consecutive parts.

According to a first variant of the invention, the interbody implant comprises a first part intended to be oriented in the posterior-anterior direction of the spine, and a second part oriented substantially perpendicular to the first part, the parts being connected by a transition portion, the front face of the second part of the implant comprising either a protrusion, making this implant a male implant, or a receiver for inserting and holding the protrusion, making this implant a female implant, in order to achieve and maintain a connection between such a male implant and such a female implant.

The male interbody implant can comprise, on the front face of its second part, a protrusion which successively comprises starting from the front face:
 a first substantially cylindrical portion having a given diameter "D1";
 a second substantially cylindrical portion having a diameter "D2" greater than "D1";
 and a substantially frustoconical portion whose initial diameter is equal to "D2" and decreases as the distance from the front face increases.

The female interbody implant can comprise, on the front face of its second part, a receiver delimited externally by elastic tongues which finish in a bulge.

The above-mentioned male interbody implant and female interbody implant may form a unit, the shape and the dimensions of the tongues of the female implant and of their bulges making them able to cooperate with the protrusion of the male implant in order to achieve and maintain a connection of the two implants.

The male interbody implant can comprise, on the front face of its second part, a protrusion whose general external shape is that of a cylinder portion whose cross section has a circumference which extends over an angle greater than 180° in such a way as to define two receiving seats in the area of its zones of connection with the front face.

The female interbody implant can comprise, on the front face of its second part, two elastic tabs, which between them define a receiver.

The above-mentioned male interbody implant and female interbody implant may form a unit, the shape and the dimensions of the elastic tabs of the female implant making them able to permit insertion of the protrusion of the male implant into the receiver, the ends of the elastic tabs being inserted into the receiving seats in order to achieve and maintain a connection of the two implants.

The invention also relates to an instrument for in situ connection of a male interbody implant and a female interbody implant of the above types, characterized in that it comprises two rods which are each equipped with means for fixing to the front face of the first part of an implant, and means for moving the rods towards one another while holding them in parallel positions.

The means for moving the rods towards one another can comprise:
 two tubes in which the rods can be inserted and blocked;
 a first transverse rod connecting the front end of the first tube to the rear end of the second tube, and a second transverse rod connecting the front end of the second tube to the rear end of the first tube, the transverse rods intersecting in the area of an articulation permitting their rotation about a common hinge pin perpendicular to the plane including the tubes;
 means for articulating the first transverse rod about a hinge pin perpendicular to the plane including the tubes, situated towards the front end of the first tube and held fixed in translation, and means for articulating the first transverse rod about a hinge pin perpendicular to the plane including the tubes, situated towards the rear end of the second tube and movable in translation in a receiving seat extending along the second tube;
 means for articulating the second transverse rod about a hinge pin perpendicular to the plane including the tubes, situated towards the front end of the second tube and held fixed in translation, and means for articulating the second transverse rod about a hinge pin perpendicular to the plane including the tubes, situated towards the rear end of the first tube and movable in translation in a receiving seat extending along the first tube;
 and means for moving the tubes towards one another in a controlled manner.

The means for moving the tubes towards one another can comprise a receiver articulated in rotation about a hinge pin perpendicular to the plane including the tubes and passing through the second transverse rod in proximity to the first tube, an externally threaded rod of which one end is inserted in the receiver and the other end is inserted in the internal space of a tube equipped with a thread corresponding to the thread of the rod, and means allowing the surgeon to turn the tube in order to regulate the depth of insertion of the rod in the tube, and a receiving seat traversed by the rod and articulated in rotation about a hinge pin perpendicular to the plane including the tubes and passing through the first transverse rod in proximity to the second tube.

The instrument can comprise a spring around the threaded rod, bearing on the receiver and the receiving seat.

According to a second variant of the invention, the interbody implant can comprise a central part and two lateral parts, which can be connected to the central part by connection means.

The connection means can comprise tapped holes formed in the end faces of the central part, and screws which can be inserted into the tapped holes and whose heads can come to rest on bearing surfaces formed on the lateral parts.

An instrument set for fitting an implant of the above type in place can comprise:
 a rod provided with means, at one of its ends, for fixing the central part of the implant;
 and two tools formed by a sheath provided at one of its ends with means permitting one of the lateral parts of the implant to be maintained there, and a screwdriver arranged inside the sheath and provided with an impression which can cooperate with the screw.

The instrument set preferably also comprises:
 a crosspiece with which it is possible to maintain the rod and the tool in determined respective angular positions during fitting of the first of the two lateral parts of the implant,
 a crosspiece with which it is possible to maintain the two tools in determined respective angular positions during fitting of the second of the lateral parts of the implant.

A tool to assist in introducing an interbody implant into a receiving seat formed in an intervertebral disc may comprise:
 a first part including a protector guide of which one end, intended to remain at the inlet of the receiving seat during the introduction, has a width "l" substantially equivalent to the height of the receiving seat and is equipped with stops intended to bear against the outer surfaces of the vertebrae;
 a second part including a distractor element placed at the end of a rod;
 a third part including a tubular element into which the rod of the second part can be inserted;
 and means permitting assembly of the three parts in a position permitting insertion of the end of the protector guide and the distractor element into the receiving seat, then disassembly of the three parts in such a way as to leave only the end of the protector guide in the receiving seat.

The means permitting assembly and disassembly of the three parts can include:
 protrusions formed on the sides of the end of the protector guide;
 receiving seats formed on the upper and lower faces of the distractor element in order to insert the protrusions of the protector guide therein;
 at least one stud formed on the anterior face of the tubular element and at least one corresponding notch formed on the posterior face of the distractor element;
 an orifice formed on the rod of the second part, a tapped hole formed on the tubular element of the third part, and a threaded element which can be inserted into the tapped hole and the orifice in such a way as to block the second and third parts relative to one another while at the same time blocking the protrusions of the protector guide in their receiving seats provided on the distractor element.

As will have been understood, the invention lies in providing a possibility of interconnection between two or more interbody implants while or after they are/have been placed separately in the degenerated disc (in other words in situ) in such a way as to form there a stable and integrated platform. Thus, in functional terms, a single implant is obtained which is made up of a plurality of segments connected to one another, without the disadvantages and risks, which would be involved in implanting a single monobloc implant by a posterior approach.

Further objects, embodiments, forms, aspects, features, benefits, and/or advantages will be apparent from the description and drawings provided herewith.

BRIEF DESCRIPTION OF DRAWINGS

The present invention will be better understood on reading the following description in which reference is made to the attached figures:

FIG. 1 shows, viewed in perspective, of two half-implants, male (FIG. 1A) and female (FIG. 1B), according to one embodiment of the present invention;

FIG. 2 shows, in a plan view (FIG. 2A) and in a side cross-sectional view along 2B-2B, the two half-implants from FIG. 1 in the connected state;

FIG. 3 shows, viewed in perspective, a second example of two half-implants, male (FIG. 3A) and female (FIG. 3B), according to the invention;

FIG. 7 shows, in perspective, an instrument to assist in fitting a half-implant according to the invention, on the one hand in the assembled state (FIG. 7A) and on the other hand in the disassembled state (FIGS. 7B, 7C, 7D).

DESCRIPTION OF SELECTED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the illustrated device, and further applications of the principles of the invention as illustrated or described herein are contemplated as would normally occur to one skilled in the art to which the invention relates.

To implant the connectable interbody implants according to one embodiment of the invention by the posterior route, the surgeon begins, in a conventional manner, by partially resecting the articular facets of the two vertebrae concerned in the operation so as to gain access to the degenerated disc. The surgeon then performs a partial discectomy so as to create fusion beds corresponding to the external shape of each of the half-implants, and the surgeon prepares the vertebral plates so as to permit subsequent fusion of the vertebrae using bone grafts enclosed by the implants which are going to be fitted. The above-described discectomy and vertebral plate preparation techniques are widely known. U.S. Pat. No. 6,174,311 issued on Jan. 16, 2001 to Branch et al., for example, describes such techniques. In one embodiment of the present invention, the two cavities formed during the partial discectomy must communicate with one another in the anterior region of the disc, in such a way as to permit connection of the half-implants in the last stage of their fitting. In one form, this technique can be performed with tools such as those described in the published PCT patent application WO-A-0128469, which is hereby incorporated by reference. Preparing the vertebral plates and maintaining the desired intervertebral distance during fitting of the half-implants can be achieved with the aid of an instrument, which will be described below. After the preparation stage, the half-implants are inserted. Two examples of pairs of such half-implants will be described herein, it being understood that these examples are nonlimiting.

Figure 1A:
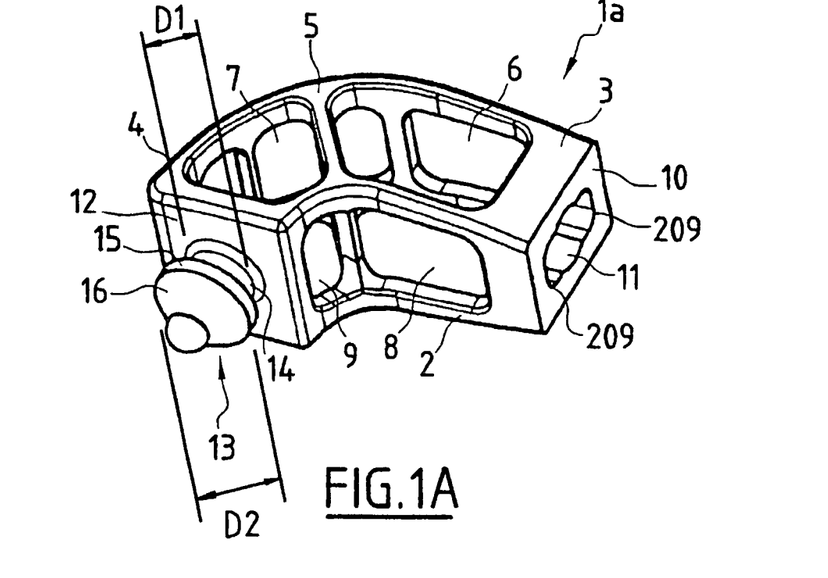
Figure 1B:
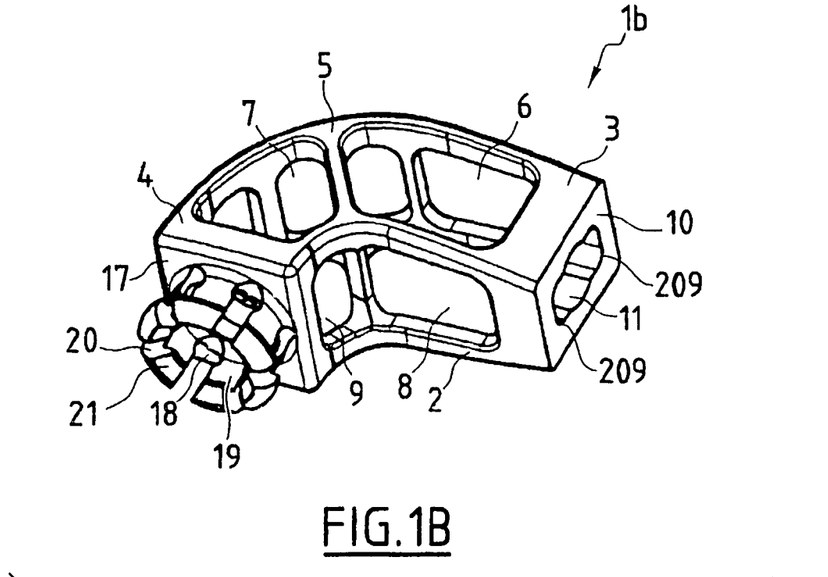

According to the first of these illustrative embodiments of the invention, the two half-implants represented in FIG. 1, namely a male half-implant 1a and a female half-implant 1b, each include an interbody cage 2 intended to enclose a bone graft or bone graft material. Each cage 2 comprises a first part 3 intended to be oriented in the posterior-anterior direction of the spine, and a second part 4 oriented substantially perpendicular to the first part 3, and being connected to the first part 3 via a transition portion 5. In one embodiment, the walls of the cage 2 at the transition portion 5 have a curvilinear shape, that is to say without sharp corners which could damage the surrounding organs during and after fitting of the half-implants 1a, 1b. In the illustrated embodiment, the cage 2 has a set of first holes 6, 7 which pass right through it between its upper surface 202 and its lower surface 204, and a set of second holes 8, 9 which pass right through the cage 2 between its side surfaces 206 and 208. These holes 6, 7, 8, 9 make it possible to insert bone graft material into the cage 2, prior to the half-implants 1a, 1b being fitted. Once implanted, the bone graft material in the cage 2 will come into contact with the vertebral plates and the remaining part of the disc. Upon bone ingrowth into the cage 2, the bone graft material aids in fusing the vertebrae together. Front face or tool engagement face 10 of the first part 3 of each half-implant 1a, 1b has a hole 11 that allows the half-implant 1a, 1b to be connected to an implantation tool, such as the ones which will be described below with reference to FIGS. 5 and 6. The holes 11 in one form are threaded so as to engage with screws on the implantation tool. As depicted in the illustrated embodiment, each hole 11 has a pair of alignment notches 209 formed on opposite sides of the hole 11, which are used to orient the half-implants 1a, 1b with the implantation tool.

As shown, the two half-implants 1a, 1b in the first illustrated embodiment have second parts 4 with different front or connection faces 12, 17. The connection face 12 of the second part 4 of the male half-implant 1a includes a protrusion 13. The protrusion 13 comprises successively, starting from connection face 12:

a first substantially cylindrical portion 14 having a given diameter "D1";
a second substantially cylindrical portion 15 having a diameter "D2" that is greater than "D1";
and a substantially frustoconical portion 16 whose initial diameter is equal to "D2" and decreases as the distance from connection face 12 increases.

The connection face 17 of the second part 4 of the female half-implant 1b includes a socket or receiver 18 for the protrusion 13 of the male half-implant 1a. The socket 18 is delimited externally by a series of elastic tongues 19. Each of the tongues 19 ends in a bulge 20 having a bevelled part 21 which cooperates with the frustoconical portion 16 upon engagement of the protrusion 13 in the socket 18, in such a way as to spread the tongues 19 apart. The tongues 19 return to their initial position after complete engagement of the protrusion 13 in the socket 18. The bulges 20 then cooperate with the connection face 12 of the male half-implant 1b and the cylindrical portions 14, 15 of the protrusion 13 so as to maintain engagement between the protrusion 13 and the socket 18. The two half-implants 1a, 1b are thus connected to form the functional equivalent of a single implant, such as is represented in FIG. 2, and they can only be disconnected by a deliberate action exerted upon their means of connection.

In the example shown, the half implants 1a, 1b, once connected together, have a horseshoe or U-shape. The height of each half implant 1a, 1b tapers or decreases progressively from second part 4 to the first part 3. In one embodiment, each half implant 1a, 1b tapers in a manners that generally matches the lordotic angle of the vertebrae. It is contemplated, however, that in other embodiments the upper 202 and lower 204 surfaces of the first part 3 can extend generally in a parallel relationship and/or can be substantially cylindrical in shape. The second parts 4 of the half implants 1a, 1b too can have various shapes, and the one shown in FIGS. 1 and 2 are only examples.

Figures 2A, 2B:
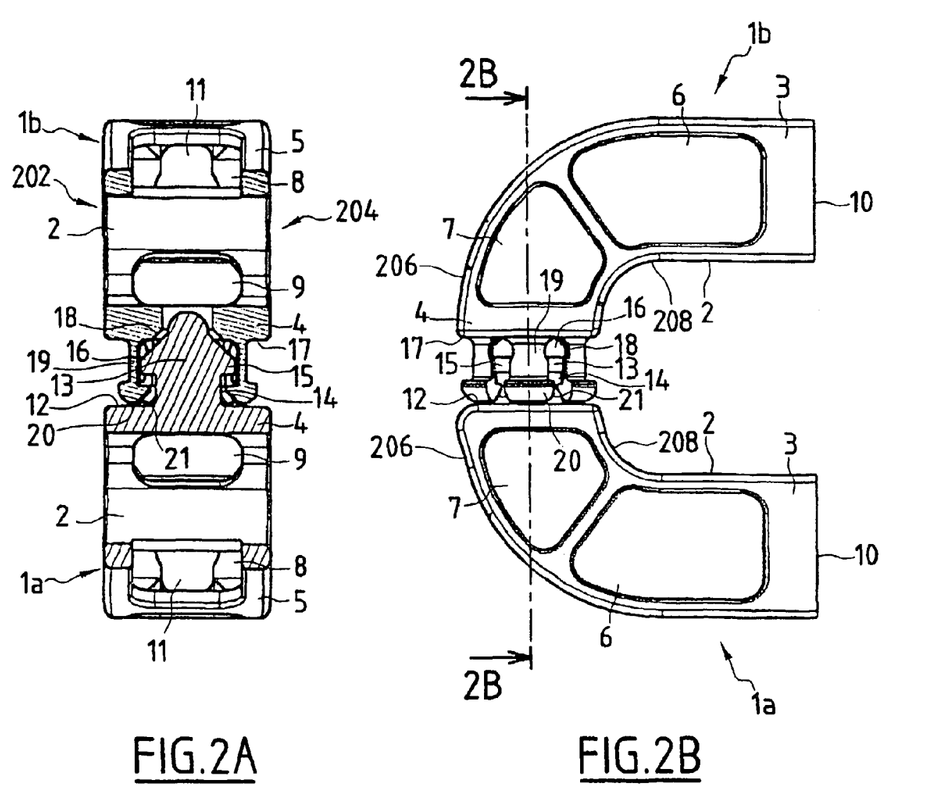
Figure 3A:
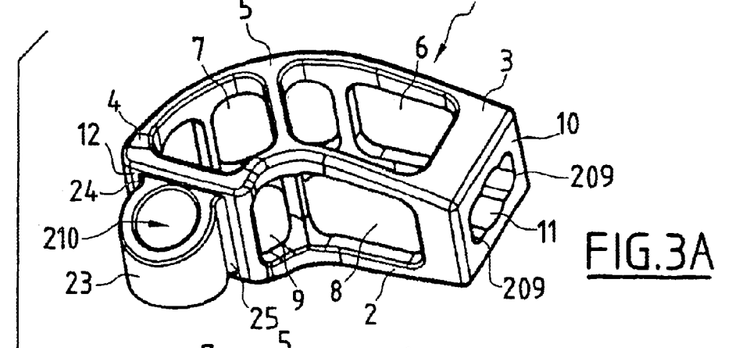
Figure 3B:
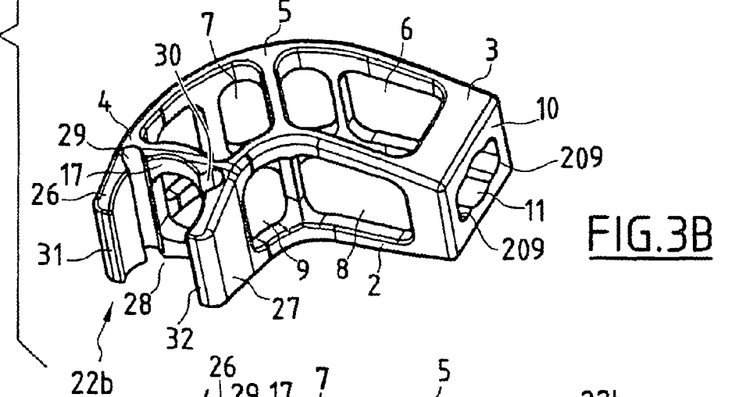

According to a second illustrated embodiment of the invention, two half-implants 22a, 22b represented in FIG. 3 are similar, in their general design, to those of the first embodiment shown in FIGS. 1 and 2. It should be noted that their common elements have been designated by the same reference numbers. As shown in FIG. 3A, the male half-implant 22a includes, on connection face 12 of its second part 4, a protrusion 23 which this time has an external shape that is generally cylindrical and, as is shown, defines a centrally located recess or cavity 210. In one form, bone graft material can be packed into cavity 210 in order to promote fusion. The cylindrical-shaped protrusion 23 has a cross section whose circumference extends over an angle that is at least greater than 180° so as to define two receiving seats or grooves 24, 25 proximal the connection face 12.

Figure 4:
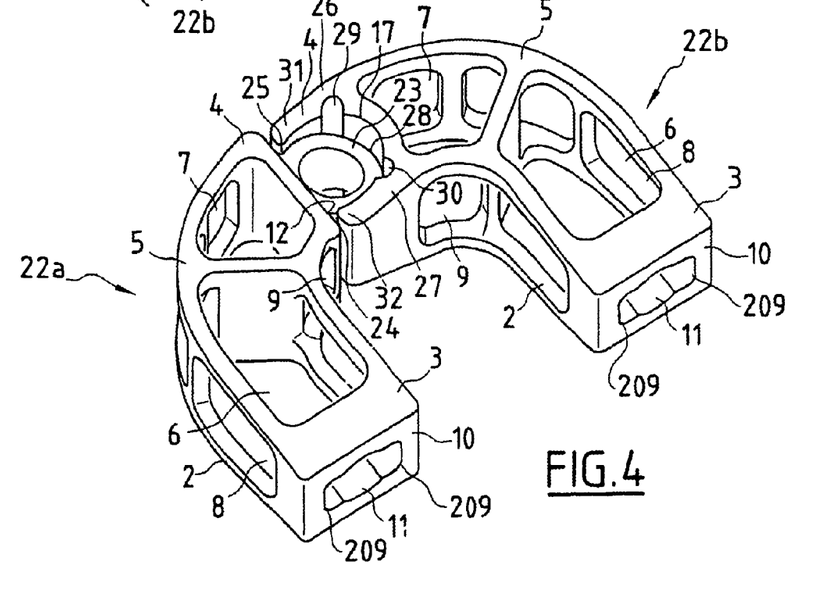
FIG. 4 shows, viewed in perspective, the two half-implants from FIG. 3 in the connected state.

The female half-implant 22b includes, on the connection face 17 of its second part 4, two elastic tabs 26, 27 which between them define an internal space 28 forming a receiver or socket for accommodating the protrusion 23 of the male half-implant 22a and for holding it there. In one form, notches 29, 30 are defined in the tabs 26, 27 proximal the connection face 17 of the female-half implant 22b, which facilitate the spreading of the tabs 26, 27 when the protrusion 23 comes into contact with them. Ends 31, 32 of the tabs 26, 27 are shaped in such a way as to be inserted in the receiving seats 24, 25 of the zones of connection of the protrusion 23 with the connection face 12 of the male half-implant 22a when the protrusion 23 is entirely engaged in the internal space 28 defined by the tabs 26, 27. In this way the protrusion 23 is firmly held in this internal space 28 and can be dislodged therefrom only by a deliberate action exerted upon the half-implants 22a, 22b. FIG. 4 shows the two half-implants 22a, 22b in the assembled position forming the functional equivalent of a single implant. As should be appreciated, the half-implants 22a, 22b illustrated in FIG. 4 allow for greater tolerance with respect to possible discrepancies in height between the two half-implants 22a, 22b when they are connected. A slight discrepancy in height between the two half-implants 22a, 22b does not compromise their connection or the maintenance of their connection.

Techniques and instrumentation for implanting the half-implants 1a, 1b, 22a and 22b will be described below with reference to FIGS. 5 and 6. Although the technique and instrumentation for inserting the half-implants 1a, 1b, 22a and 22b will be described below with reference to half-implants 1a and 2b, it should be understood that the below described techniques and instrumentation can be used with half-implants 22a and 22b as well as other types of half-implants. Before the half-implants 1a, 1b are inserted, the disc space is prepared in the manner as described above. The insertion of the of the half-implants 1a, 1b is then performed by attaching the half-implants 1a, 1b to the end of rods that are inserted in the holes 11 of the front faces 10 of their first parts 3, and by connecting the half-implants 1a, 1b together by manipulation of these rods. The ends of the second parts 4 of the half-implants 1a, 1b are then moved towards one another in order to connect them to one another in situ. Instrument 33 and 33' (implantation tool) allow for the connection of the half-implants 1a, 1b in such a manner. The instrument 33, 33' allows the half-implants 1a, 1b to be moved towards each other in a gradual and controlled manner while constantly keeping them in a parallel orientation. This improves the chance that the insertion of the protrusion 13, 23 of the male element 1a, 22a in the corresponding receiving seat 18, 28 of the female element 1b, 22b is effected under optimum conditions.

Figure 5:
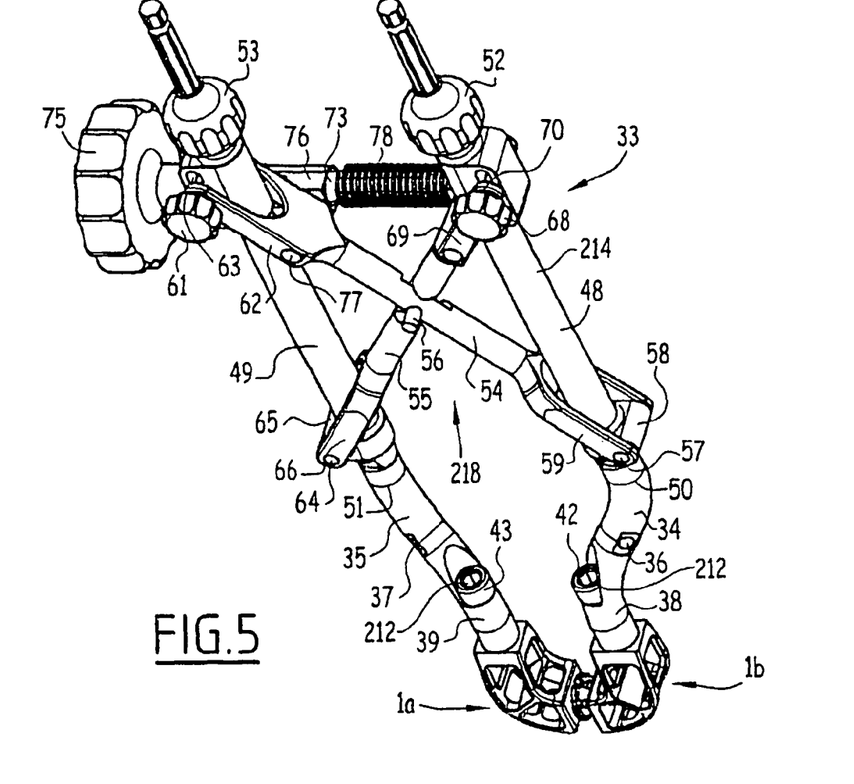
FIG. 5 shows, viewed in perspective, an instrument designed for the positioning and connection of two half-implants according to the invention.
Figure 6:
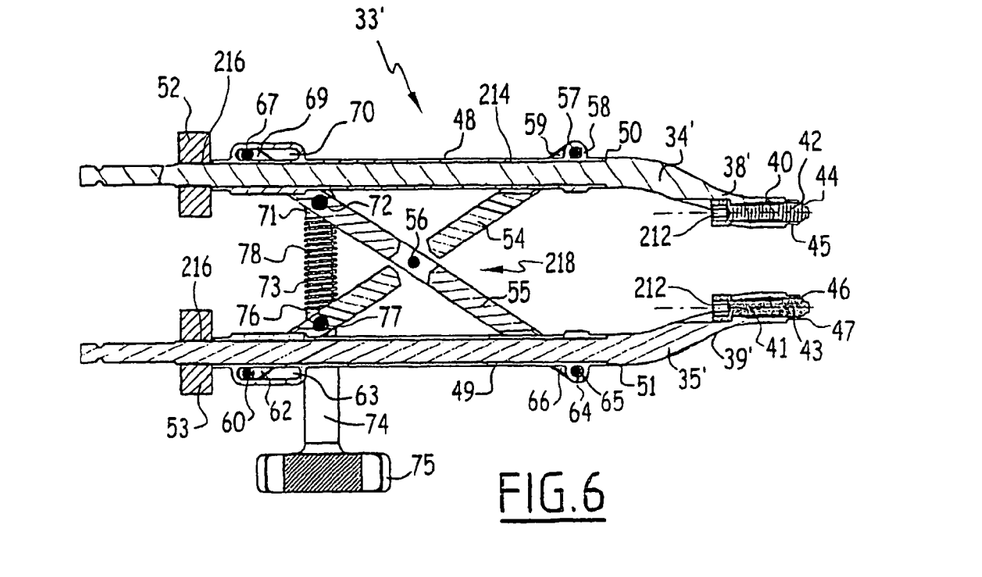
FIG. 6 shows, in a plan view and longitudinal section, a variant of the instrument in FIG. 5.

FIG. 5 illustrates one embodiment for the instrumentation 33 that is used to implant the half-implants 1a, 1b, and FIG. 6 illustrates instrumentation 33' according to another embodiment. It should be noted that instrumentation 33 and 33' share a number of common features. For the sake of brevity and clarity, instrumentation 33 and 33' will be discussed together below with particular reference to instrumentation 33. Although instrumentation 33 will be referenced below, it should be understood that the same description for instrumentation 33 applies as well as to instrumentation 33, with any notable distinctions between the two embodiments being highlighted. With reference to the embodiment illustrated in FIG. 5, the instrumentation 33 includes two rods 34, 35 composed of several parts that are connected together by systems which, for example, can include slots or holes and fixed or detachable indexing pins. In the FIG. 5 embodiment, the parts of the rods 34, 35 are connected together with detachable indexing pins 36, 37. It is contemplated, however, that the rods 34, 35 can each be made from a single part. For example, in the embodiment illustrated in FIG. 6, the instrumentation 33' includes two rods 34', 35', each having a unitary construction.

The rods 34, 35 are intended to support the half-implants 1a, 1b, when the half implants 1a, 1b are connected together. However, the rods 34, 35 can also be used alone and independently by the surgeon for manipulating the half-implants 1a, 1b during insertion of the half-implants 1a, 1b in the receiving cavities (or seats) hollowed out in the degenerated disc. To fix the half-implants 1a, 1b in the illustrated embodiment, the rods 34, 35 each have a bent end part 38, 39 that defines an orifice 40, 41 in which a screw 42, 43 is received. In the embodiment illustrated in FIG. 5, these bent parts 38, 39 have a skewed shape in which the bent parts 38, 39 bend away from a plane defined by the rods 34, 35. By skewing bent parts 38 and 39 in such a manner, the area around the orifices 40, 41 is freed so that the screws 42, 43 can be easily accessed. However, it should be appreciated that the bent parts 38, 39 can have a planar arrangement. For instance, in the embodiment illustrated in FIG. 6, bent parts 38' and 39' are oriented in the same plane as the rest of the rods 34', 35'. At the extremity of the end part 38, 39, each rod 34, 35 has tabs 44, 45, 46, 47 intended to be inserted in receiving seats or alignment notches 209 formed on the sides of the holes 11 provided on the front faces 10 of the half-implants 1a, 1b, or in separate receiving seats specially designed for this purpose. These tabs 44, 45, 46, 47 make it possible to fix the half-implants 1a, 1b on the rods 34, 35 in defined orientations. The screws 42, 43, cooperating with the threads formed on the surfaces delimiting the holes 11 in the half-implants 1a, 1b, permit this fixation. The bent portions 38, 39 of the rods 34, 35 permit access to heads 212 of the screws 42, 43 so that these can be tightened and loosened. It goes without saying that the device for fixing the half-implants 1a, 1b which has just been described is but one example and that the skilled person can imagine other examples which would satisfy the same functions.

After the half-implants 1a, 1b have been secured to the rods 34, 35, the rods 34, 35 are introduced into a positioning device 214 that allows them to be held in a position in which the rods 34, 35 are oriented parallel with respect to one another. The positioning device 214 also makes it possible to regulate the spacing of the rods 34, 35 from each other so that the surgeon can bring the half-implants 1a, 1b towards each other and connect the half-implants 1a, 1b, after the half-implants 1a, 1b have been fitted in the receiving cavities hollowed out in the disc. In the example shown in FIGS. 5 and 6, the positioning device 214 in the first instance includes two tubes 48, 49 in which the rods 34, 35 are inserted. The rods 34, 35 are secured in the tubes 48, 49 by stop members or bearings 50, 51 (or any other functionally equivalent device) formed on the rods 34, 35 on which the tubes 48, 49 come into abutment, and by internally threaded rings 52, 53 which, by cooperating with corresponding threads 216 formed on the ends of the rods 34, 35, press the stop members 50, 51 against the tubes 48, 49.

The tubes 48, 49 are connected to one another by means of an articulated device 218. The articulated device 218 in the first instance includes two transverse rods 54, 55, which are pivotally coupled to one another to permit their rotation about a common hinge pin 56, which extends perpendicular to the plane that includes the tubes 48, 49. The first transverse rod 54 is pivotally coupled to the distal or front end of the first tube 48 (that is to say the end nearest the half-implant 1a) about a hinge pin 57 that extends parallel to the common hinge pin 56 of the transverse rods 54, 55. Hinge pin 57 is held in a receiving seat 58 which is fixed to the first tube 48 and which prohibits any movement thereof in translation relative to the first tube 48. The pivoting of the first transverse rod 54 about the hinge pin 57 is ensured by a stirrup 59. As shown, the stirrup 54 of the first transverse rod 54 extends around opposite sides of tube 48. The first transverse rod 54 is also coupled to the proximal or rear end of the second tube 49 (that is to say the end farthest from the half-implant 1b) about a hinge pin 60. A knurled wheel 61 is threadedly coupled to hinge pin 60. Hinge pin 60 extends in parallel relationship with respect to the common hinge pin 56 of the transverse rods 54, 55. Hinge pin 60 is coupled with the first transverse rod 54 by a stirrup 62, which can pivot about hinge pin 60. Hinge pin 60 is able translationally move in a receiving seat or slot 63 that extends along the second tube 49. The second transverse rod 55 is similarly pivotally coupled to the front end of the second tube 49 about a hinge pin 64. Hinge pin 64 is held in a receiving seat 65 fixed to the second tube 49. As shown, rod 55 has a stirrup 66 that is received around tube 49, and the stirrup 66 is coupled to hinge pin 64. The second transverse rod 55 is also pivotally coupled to the rear end of the first tube 48 with a hinge pin 67. A knurled wheel 68 is threadedly coupled to the hinge pin 67. Hinge pin 67 is coupled to the second transverse rod 55 by a stirrup 69, which can pivot about hinge pin 67. Hinge pin 67 is able to translationally move in a receiving seat or slot 70 that extends along the first tube 48. The use of knurled wheels 61, 68 and the threaded hinge pins 60, 67 cooperating with corresponding threads formed in the stirrups 62, 69 ensures simple assembly and disassembly of the device 214.

Device 214 includes a receiver 71 that rotates about a hinge pin 72 that extends parallel to the other axes of rotation for hinge pins 56, 57, 60, 64 and 67, which were mentioned above. Hinge pin 72 passes through the second transverse rod 55 in proximity to the first tube 48. One end of an externally threaded rod 73 is inserted and fixed in receiver 71. The other end of the threaded rod 73 is inserted in the internal space of a tube 74 equipped with a thread corresponding to the thread of the rod 73. Tube 74 is equipped with a knurled wheel 75 that allows the surgeon to turn it and thereby regulate the position of the rod 73 relative to the tube 74. As shown, a receiving seat 76 is rotatably coupled a hinge pin 77 that passes through the first transverse rod 54 in proximity to the second tube 49. Receiving seat 76 is able to rotate about an axis that is extends parallel to the axes of rotation of hinge pins 56, 57, 60, 54, 67 and 72, which were mentioned above. The threaded rod 73 passes through receiving seat 76.

After the whole instrument 214 has been assembled, the surgeon is able to move the two rods 34, 35 supporting the half-implants 1a, 1b towards or away from each other by turning the knurled wheel 75 in such a way as to regulate the penetration depth of the rod 73 in the tube 74, which determines the spacing of the rods 34, 35. Also, the ability of the transverse rods 54, 55 to rotate about the various hinge pins 56, 57, 60, 64, 67, 72, 77, and the ability of translational movement of hinge pins 60 and 67 in receiving slots 63 and 70, mean that this movement of the rods 34, 35 towards or away from each other is effected while ensuring permanent parallel positioning of the rods 34, 35. The half-implants 1a, 1b can therefore be moved towards each other in the direction most favourable to their proper connection.

A spring 78 is provided about the threaded rod 73 and bears on receiver 71 and receiving seat 76. The spring 78 makes it possible to increase the rigidity of the assembled instrument because the spring 78 tends to space the rods 34, 35 apart from one another in order to reduce the play which may exist between the different components controlling the spacing of the rods 34, 35. Reduction of this play can make use of the instrument 214 easier.

One should appreciate that variations can be made to the design of the positioning device 214 for controlling the movement of the two rods 34, 35. For example, it would be conceivable to move the rods 34, 35 together using an elastic device which can be controlled by a clamp or by simple manual pressure. The threaded-tube and threaded-rod device which has been described has the advantage of allowing easily controlled progressive clamping of the rods 34, 35, and permanent holding of a selected relative position of the rods 34, 35, permitting, if necessary, the half-implants 1a, 1b to move towards each other in several stages without requiring the surgeon to manually holds the rods 34, 35 in order to keep the spacing of the rods 34, 35 constant.

Once the half-implants 1a, 1b have been connected to one another, the rings 52, 53 are removed so as to allow disconnection of the rods 34, 35 from the rest of the positioning device 214. The screws 42, 43 are then loosened so as to disconnect the rods 34, 35 from the half-implants 1a, 1b whose implantation is then complete.

Figure 8A:
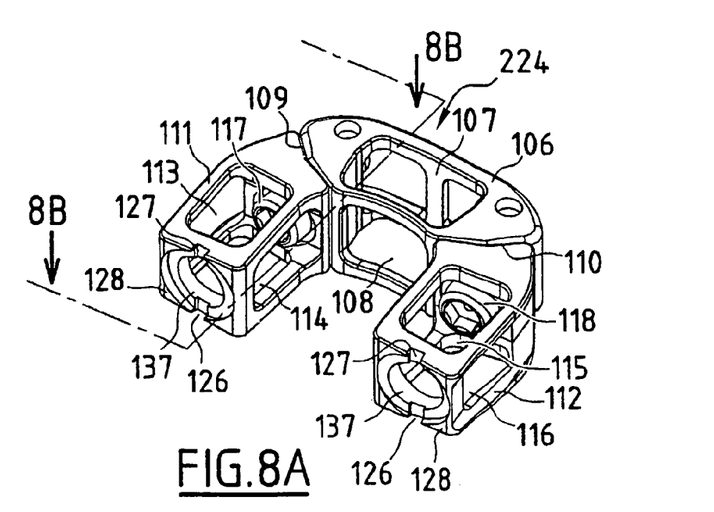
Figure 8B:
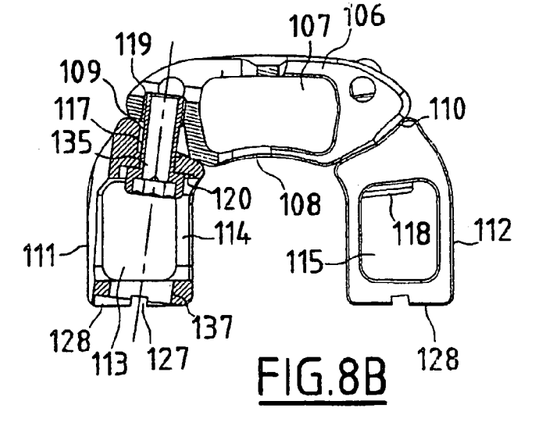

According to another variation of the present invention, the interbody implant no longer comprises two parts, but three parts, namely a central part and two lateral parts which are fixed together more or less rigidly depending on the wishes of the user. An illustrative embodiment of this variation is shown in FIGS. 8A and 8B. In implant assembly 224, a central part 106 of the implant 224 is in the form of a cage, which has apertures 107 through its upper and lower faces and apertures 108 through its lateral faces, in such a way as to permit a bone graft material to be inserted into the central part 106 prior to its fitting. The central part 106 has a general shape that is slightly arched in order to match the shape of the receiving cavity that has been formed in the disc. The ends of the central part 106 include end faces 109, 110 oriented obliquely in relation to the general direction of the central part 106, so as to be easily accessible from the outside when the central part 106 is in place in its receiving cavity. The implant 224 also includes two lateral parts 111, 112 in the form of cages, which have apertures 113, 114, 115 and 116 for receiving bone graft material. The lateral parts 111, 112 are connected to the central part 106 by way of screws 117, 118, which can be inserted into tapped holes 119 formed in the end faces 109, 110 of the central part 106, and the heads of which engage bearing surfaces 120 formed on the lateral parts 111, 112. This assembling of implant 224 by means of screws 117, 118 gives it great rigidity.

Figure 9:
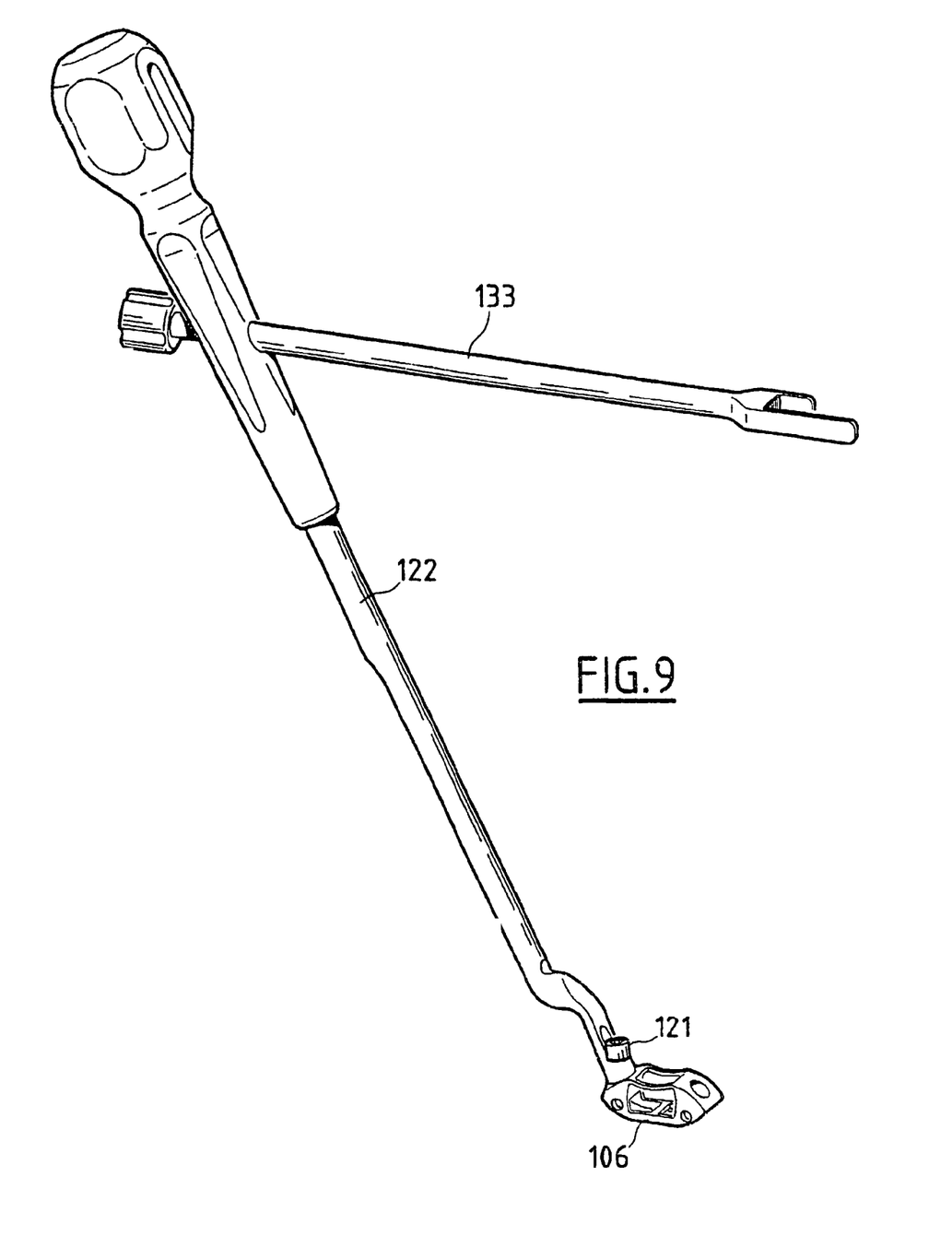
FIG. 9 shows, in perspective, a rod which is used when fitting the implant in FIG. 8.

To fit implant 224 in place, the following described techniques can be used. The central part 106 is fixed with the aid of a screw 121 (which, as is shown, can be identical to one of the screws 117, 118 which will be used for assembling the implant 224) to the end of a rod 122 which is designed, for example, in a manner similar to one of the rods 34, 35 of the instrument set shown in FIGS. 5 and 6, as can be seen from FIG. 9. The surgeon then introduces the central part 106 into the receiving cavity that was formed beforehand in the damaged disc. Of course, it should be appreciated that other means of fixing other than the screw 121 are conceivable.

Figure 10:
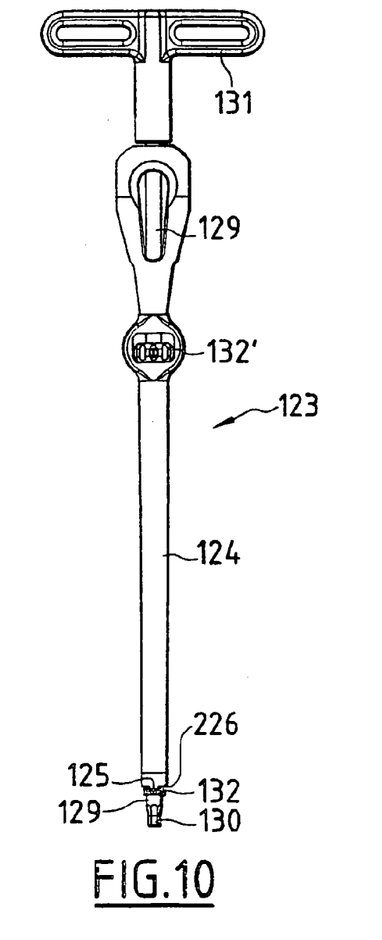
FIG. 10 shows a tool which is also used during this fitting.

In the following stage, the surgeon uses a tool 123, shown in FIG. 10, which is made up of two main parts:

a sheath 124 provided at one of its ends with means permitting one of the lateral parts 111, 112 of the implant to be maintained there, for example comprising two studs or tabs 125 which cooperate with two corresponding notches 126, 127 formed on the anterior face 128 of each of the lateral parts 111, 112; and a screwdriver 129 extending inside and through the sheath 124; one of its ends is provided with an impression or head 130 which can engage with the screw 117, and the other end is provided with a grip handle 131 that allows the surgeon to turn the screwdriver 129.

In the example shown, a tube 132 is positioned inside the sheath 124 such that there is only a slight clearance between the tube 132 and the sheath 124 so that the tube 132 is able to move inside the sheath 124. As depicted in FIG. 10, the tube 132 in the sheath 124 has externally threaded end 226, and the tube 132 can be rotated through a knurled wheel 132', which is attached to the tube 132. When rotated, the threaded end 226 of the tube 132 is used to engage with a corresponding threading formed in a bore 137 of the anterior face 128 of a lateral part 111, 112 of the implant 224. One could of course conceive of other means for maintaining the lateral part 111, 112 of the implant 224 connected to the sheath 124. As shown, the screwdriver 129 is slidably received inside tube 132 such that the screwdriver 129 is able to rotate inside tube 132 and tighten screw 117.

Figure 11:
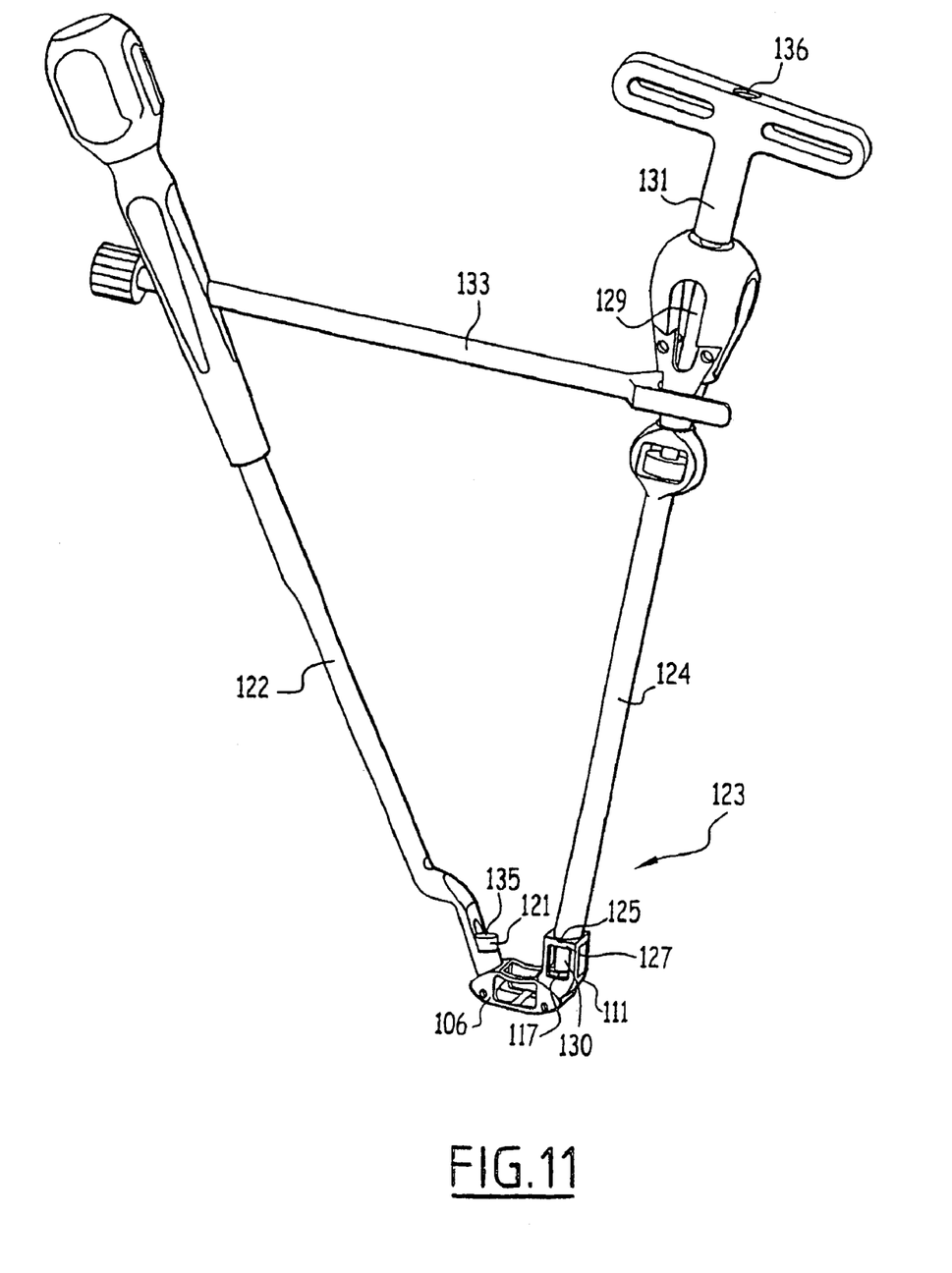
FIGS. 11 and 12 show, in perspective, two stages of this fitting.

Referring to FIG. 11, lateral part 111 of the implant 224 is secured to the threaded end 226 of the tube 132 in tool 123, and the screw 117 is placed at the end of the screwdriver 129 of the tool 123. Lateral part 111 of the implant 224 is then inserted into the receiving cavity formed in the disc in order to move it to the central part 106, which is still fixed to the rod 122. Lateral part 111 is positioned to bring the screw 117 in alignment with the tapped hole 119 formed in the face 109 of the central part 106. To facilitate this positioning, in one embodiment, a calibrated crosspiece 133 is used to maintain the rod 122 and the tool 123 in a suitable angular orientation. The crosspiece 133 also makes it possible to obtain a precise placement of the central part 106 of the implant in its receiving cavity. When the desired positioning is obtained, the surgeon turns the screwdriver 129 in order to tighten the screw 117 so as to secure the central part 106 and the lateral part 111. FIG. 11 illustrates the configuration of the implant assembly 224 at the end of this stage (the disc and its surrounding area have not been shown for the sake of clarity).

Figure 12:
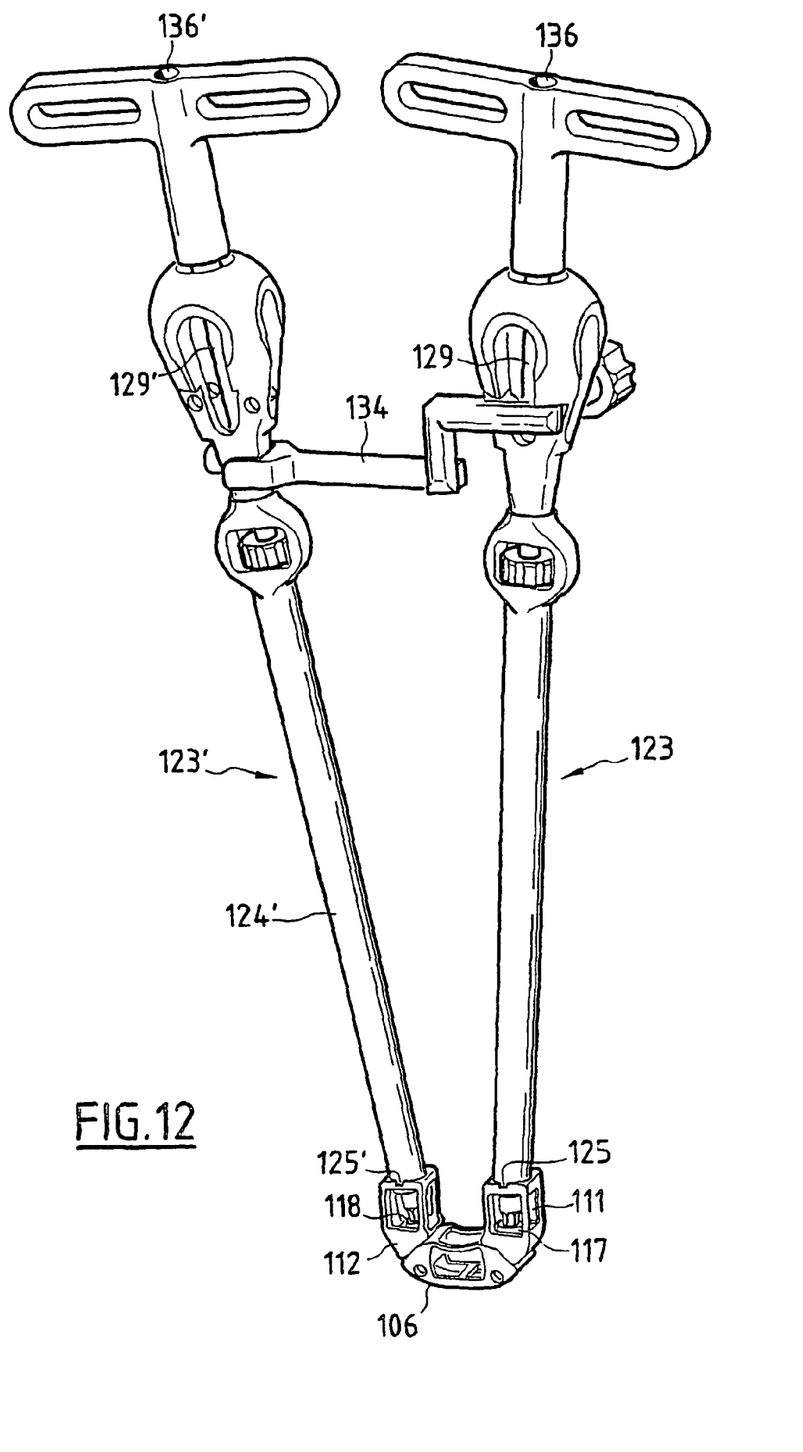

After the lateral part 117 is attached to the central part 106, the rod 122 is then disconnected from the central part 106 of the implant 224 by loosening the screw 121. The other lateral part 112 of the implant 224 is attached at the threaded end 226 of a tool 123', which is identical to the previous tool 123. Screw 118 is placed at the end of the screwdriver 129' in the tool 123'. With tool 123', lateral part 112 is moved to engage the end face 110 of the central part 106 that was disengaged from rod 122. The other lateral part 112 is then secured to the central part 106 with screw 118 in the same manner as described above. In one embodiment, a crosspiece 134 is used to maintain the angular positioning of the two tools 123, 123'. FIG. 12 shows the assembly 224 at the end of this stage. Once the other lateral part 112 has been fixed, the two tools 123, 123' are withdrawn by rotation of the knurled wheels 132' making it possible to detach the tubes 132 from the bores 137 of the anterior faces 128 of the lateral parts 111, 112.

When the two tools 123, 123' are removed, the insertion of the implant 224 is thus completed. In one embodiment, to make it easier to align the screws 117, 118 with the tapped holes 119 of the central part 106, a metal wire is passed through a central aperture 135 (FIG. 8B) in the screw 121 that connects rod 122 to the end face 109 of the central part 106. The wire is further passed through the tapped hole 119 of the other end face 110 of the central part 106. The screws 117, 118 and the screwdrivers 129, 129' are themselves provided with central apertures 135, 136, 136' in which the wire can be passed through. With the wire passing through the screws 117, 118 and the screwdrivers 129, 129', the end of the portion of the wire extends from tapped hole 119 so that the screws 117, 118 are correctly guided towards the tapped holes 119. After the rod 122 has been withdrawn, the other end of the wire emerging from the central part 106 becomes accessible, and the screw 118 carried by the screwdriver 129' of the tool 123' can be engaged on this end of the wire. After the implant 224 has been fitted, the wire is removed.

The above-described embodiment in which the implant includes three parts has at least the following advantages:
  at each operation, only a component of relatively small dimensions is inserted into the body of the patient; this entails a less invasive approach; it is no longer necessary to remove as many stabilizing elements like the articular facets of the vertebrae, and it is possible to dispense with sectioning the muscles, and instead they need only be moved aside: recovery is therefore quicker; and
  the connection operations take place closer to the openings of the cavity formed in the disc, thus in a zone which is visible to the surgeon, making it easier to fit the implant;
  moreover, this permits a connection by screws, thus one which is rigid, reliable and relatively easy to effect.

The connection means which have been described and shown for this illustrative embodiment of the invention are not exclusive, and the person skilled in the art will be able to adopt other connection means analogous, for example, to those described for the previously described implant variants made up of two parts. The degree of rigidity sought for the assembled implant will be a criterion in choosing the method of connecting the different parts. The person skilled in the art will be readily able to adapt the configurations of the different parts of the implant to this effect, and of the tools used to fit them, by drawing inspiration from what has been set out in this description.

When the implants (1a, 1b), (22a, 22b), (106, 111, 112) are being put in place, it is possible for the surgeon to use spacer tool 78, which aids in introducing the parts of the implants (1a, 1b), (22a, 22b), (106, 111, 112) into their respective receiving cavities. Tool 78 maintains the space between the vertebrae concerned, while at the same time protects the surrounding area, in particular the spinal nerves, which is very important in the posterior lumbar region where the implants (1a, 1b), (22a, 22b), (106, 111, 112), according to one embodiment, are intended to be implanted.

Figures 7, 7A, 7B, 7C, 7D:
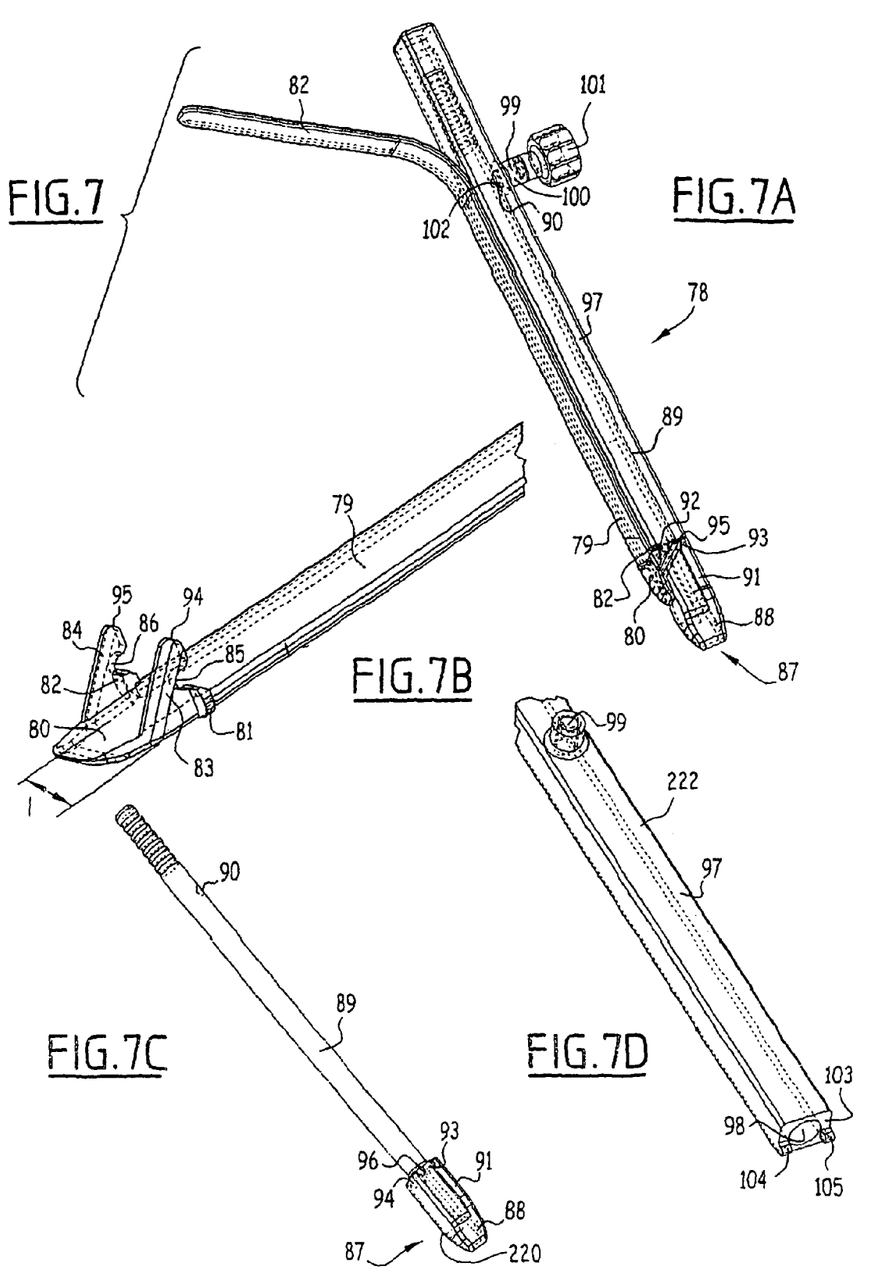

This tool 78 is made up of three parts. The first part is a protector guide 79 of which one end 80 is intended to be positioned at the inlet of one of the receiving cavities formed in the vertebrae for the half-implants (1a, 1b), (22a, 22b), (106, 111, 112) during their introduction. The rest of tool 78 is designed to protect the surrounding area of the work zone and to permit easy manipulation by the surgeon, for example, as is shown, in the form of a straight part finishing in a bent part 82 set outwards from the operating site. As shown in FIG. 7B, end 80 of tool 78 has a width "l" largely equivalent to the height of the receiving cavities formed in the disc for fitting of the implants (1a, 1b), (22a, 22b), (106, 111, 112). It is equipped with stops 81, 82 that are configured to bear against the outer surfaces of the vertebrae upon introduction of the instrument into the receiving cavity, so as to limit its penetration to the necessary length. End 80 of the protector guide 79 is also equipped on its sides with two protrusions 83, 84 that have a generally triangular shape and are equipped with posterior notches 85, 86 whose function will be explained below.

The second part of tool 78 is a distractor element 87, which is configured to support the end 80 of the protector guide 79 upon its insertion into the receiving cavity formed in the vertebrae for the implant (1a, 1b), (22a, 22b), (106, 111, 112). The distractor element 87 is tapered at its front end 88 to facilitate its introduction into the receiving cavity formed in the vertebrae. The distractor element 87 is placed at the end of a rod 89 which has, on its cylindrical lateral wall, an orifice 90 whose function will be explained below. Engagement seats are formed in the upper face 91 and lower face 220 of the distractor element 87 for the protrusions 83, 84 of the protector guide 79. These engagement seats are each delimited on the one hand by a stud 92 which is received in one of the posterior notches 85, 86 in the protrusions 83, 84 of the and on the other hand by a hollowed-out portion 93 which receives the free corner 94, 95 of one of the protrusions 83, 84 by blocking its movements towards the front of the distractor element 87. The distractor element 87 also has, on its rear face, two notches 96 whose function will be explained below.

The third part of tool 78 is a tubular element 97, with rectangular cross-section in the example shown, and provided with a receiving cavity 98 permitting insertion of the rod 89 of the second part of the tool 78. One of the lateral surfaces 222 of the tubular element 97 has a tapped hole 99 in which a threaded element 100 with a knurled wheel 101 is threaded. End 102 of the threaded element is configured to penetrate into the orifice 90 of the rod 89 of the distractor element 87 when tool 78 is assembled. The position of the tapped hole 99 is determined accordingly. Anterior face 103 of the tubular element 97 has studs 104, 105 that are configured to be inserted in the notches 94 of the posterior face of the distractor element 87. The studs 104, 105 and the notches 94 make it possible to regulate the relative positions of the distractor element 87 and the tubular element 97 in such a way that orifice 90 in the distractor element 87 and the tapped hole 99 in the tubular element 97 are automatically aligned with one another upon assembly of the tool 78. It would of course be possible to provide just one stud 102, 103 and a single notch 94 or any other means of establishing suitable relative positions of the distractor element 87 and the tubular element 97 when assembling the tool 78.

Tool 78 is assembled as follows. In a first stage, the protector guide 79 and the distractor element 87 are placed one on top of the other, with the triangular protrusions 83, 84 of the protector guide 79 inserted in the corresponding receiving seats of the distractor element 87. In a second stage, the rod 89 of the distractor element 87 is inserted in the receiving cavity 98 of the tubular element 97 and secured inside the receiving cavity 98 with the threaded element 100, which is made to penetrate into orifice 90. The triangular protrusions 83, 84 are thus secured in their respective receiving seats on the distractor element 87 by the anterior face 103 of the tubular element 97, and the whole tool is thus stabilized, with the protector guide 79 held along the tubular element 97. The distractor element 87 and the end 80 of the protector guide 79 are then inserted in a receiving cavity previously hollowed out in the degenerated disc, in such a way as to establish the exact interdiscal distance necessary for introducing the corresponding implant (1a, 1b), (22a, 22b), (106, 111, 112), which distance is substantially equal to "l", and to complete the preparation of the receiving seat surfaces. The threaded element 100 is then loosened, which allows the third part of the tool to be withdrawn, then the second part, so that only the end 80 of the protector guide 79 is left remaining in the receiving cavity. A part of implant (1a, 1b), (22a, 22b), (106, 111, 112) is then inserted in the receiving cavity. With the end 80, it is possible to maintain the desired interdiscal space during this introduction, while the rest of the protector guide 79, which extends outside the receiving cavity for the implant (1a, 1b), (22a, 22b), (106, 111, 112), makes it possible to move aside and protect the organs of the patient which are situated on the path of insertion of the implant (1a, 1b), (22a, 22b), (106, 111, 112).

It goes without saying that detailed modifications can be made to the various parts of the tool 78 (in particular as regards the means of joining its various parts), provided that the essential functions of its various elements are retained. This tool can also be used to assist in placing interbody implants having a configuration different than that of the implants (1a, 1b), (22a, 22b), (106, 111, 112) described herein.

While the invention has been illustrated and described in detail in the drawings and foregoing description, the same is to be considered as illustrative and not restrictive in character, it being understood that only the preferred embodiment has been shown and described and that all changes, modifications, and equivalents that come within the spirit of the inventions described herein and/or defined by the following claims are desired to be protected.

What is claimed is:

1. Intersomatic implant for inserting and maintaining a bone graft in place in a receiving seat formed in a disc with a view to obtaining intervertebral fusion, comprising:
   a plurality of interbody cages, each of said interbody cages defining a substantially open hollow interior and including upper and lower vertebral engaging surfaces and an opening passing through said upper and lower vertebral engaging surfaces and into communication with said hollow interior to facilitate fusion with adjacent vertebrae; and
   means for in situ connection of two consecutive ones of said interbody cages, and in that the implant as a whole comprises a horseshoe-shaped or U-shaped implant assembly having two generally linear lateral portions extending substantially parallel to one another in an anterior-posterior direction and a central portion defining a generally semi-circular curvature extending between said generally linear lateral portions.

2. Intersomatic implant according to claim 1, characterized in that each of said two consecutive ones of said interbody cages includes either a protrusion, making this implant a male implant, or a receiver for inserting and holding said protrusion, making this implant a female implant, in order to achieve and maintain a connection between said male implant and said female implant.

3. The intersomatic implant according to claim 2 wherein the protrusion of the male implant successively comprises;
   a first substantially cylindrical portion having a given diameter "D1";
   a second substantially cylindrical portion having a diameter "D2" greater than "D1"; and
   a substantially frustoconical portion whose initial diameter is equal to "D2" and decreases toward a distal end of the protrusion.

4. The intersomatic implant according to claim 3, wherein:
   the receiver of the female implant is delimited externally by elastic tongues which finish in a bulge; and
   the shape and the dimensions of the tongues of the female implant and of their bulges making them able to cooperate with the protrusion of the male implant in order to achieve and maintain a connection of the male and female implants.

5. The intersomatic implant according to claim 2, wherein the receiver of the female implant includes a plurality of elastic tongues, each of said elastic tongues including an end defining an inwardly extending bulge.

6. The intersomatic implant according to claim 2, wherein the protrusion of the male implant has a general external shape of a cylinder portion whose cross section has a circumference which extends over an angle greater than 180° in such a way as to define two receiving seats.

7. The intersomatic implant according to claim 6, wherein:
   the female implant includes two elastic tabs which between them define said receiver; and
   the shape and the dimensions of the elastic tabs of the female implant making them able to permit insertion of the protrusion of the male implant into the receiver, the ends of said elastic tabs being inserted into the receiving seats in order to achieve and maintain a connection of the male and female implants.

8. The intersomatic implant according to claim 2, wherein the female implant includes two elastic tabs which between them define said receiver.

9. The intersomatic implant according to claim 1, further comprising bone graft material positioned within each of said interbody cages to further facilitate fusion with the adjacent vertebrae.

10. The intersomatic implant according to claim 1, wherein each of said consecutive ones of said interbody cages includes one of said lateral portions of said implant assembly and also includes an arc-shaped portion extending along approximately one-quarter of a circle, said arc-shaped portions of said interbody cages interconnected to one another by said means for in situ connection to define said semi-circular curvature of said central portion of said implant assembly.

11. An interbody implant for implanting between adjacent vertebrae, comprising:
a male implant having an engagement protrusion extending therefrom;
a female implant defining a socket; and
wherein said male implant comprises a first interbody cage and said female implant comprises a second interbody cage, each of said first and second interbody cages defining a substantially open hollow interior and including upper and lower vertebral engaging surfaces and an opening passing through said upper and lower vertebral engaging surfaces and into communication with said hollow interior to facilitate fusion with the adjacent vertebrae; and
wherein said protrusion of said male implant is engaged in said socket of said female implant; and
wherein the interbody implant comprises a horseshoe-shaped or U-shaped implant assembly having two generally linear lateral portions extending substantially parallel to one another in an anterior-posterior direction and a central portion defining a generally semi-circular curvature extending between said generally linear lateral portions.

12. The implant of claim 11, wherein said socket is defined by a plurality of elastic tongues.

13. The implant of claim 11, wherein said protrusion has a cylindrical shape and said socket has a cylindrical shape.

14. The implant of claim 11, further comprising bone graft material positioned within each of said first and second interbody cages to further facilitate fusion with the adjacent vertebrae.

15. The implant of claim 11, wherein each of said first and second interbody cages includes one of said lateral portions of said implant assembly and also includes an arc-shaped portion extending along approximately one-quarter of a circle, said arc-shaped portions of said interbody cages interconnected to one another by engagement of said protrusion in said socket to define said semi-circular curvature of said central portion of said implant assembly.

16. Intersomatic implant for inserting and maintaining a bone graft in place in a receiving seat formed in a disc with a view to obtaining intervertebral fusion, comprising:
a plurality of interbody cages, each of said interbody cages defining a substantially open hollow interior and including upper and lower vertebral engaging surfaces and an opening passing through said upper and lower vertebral engaging surfaces and into communication with said hollow interior to facilitate fusion with adjacent vertebrae; and
means for in situ connection of two consecutive ones of said interbody cages, and in that the implant as a whole defines a horseshoe-shaped or U-shaped implant assembly; and
wherein the implant assembly includes a first of said interbody cages and a second of said interbody cages, each of said first and second interbody cages including a lateral portion oriented in a posterior-anterior direction and an arc-shaped portion extending along approximately one-quarter of a circle, said arc-shaped portion of said first interbody cage connected to said arc-shaped portion of said second interbody cage by said means for in situ connection to provide said horseshoe-shaped or U-shaped implant assembly.

17. An interbody implant for implanting between adjacent vertebrae, comprising:
a male implant having an engagement protrusion extending therefrom;
a female implant defining a socket; and
wherein said male implant comprises a first interbody cage and said female implant comprises a second interbody cage, each of said first and second interbody cages defining a substantially open hollow interior and including upper and lower vertebral engaging surfaces and an opening passing through said upper and lower vertebral engaging surfaces and into communication with said hollow interior to facilitate fusion with the adjacent vertebrae; and
wherein said protrusion of said male implant is engaged in said socket of said female implant; and
wherein each of said first and second interbody cages includes a a lateral portion oriented in a posterior-anterior direction and an arc-shaped portion extending along approximately one-quarter of a circle, said arc-shaped portion of said first interbody cage connected to said arc-shaped portion of said second interbody cage by engagement of said protrusion of said male implant in said socket of said female implant; and
wherein said first and second interbody cages are interconnected to provide a U-shaped implant assembly.

18. An interbody implant for implantation between adjacent vertebrae, comprising:
a first interbody cage having a protrusion extending therefrom;
a second interbody cage defining a socket;
said first and second interbody cages each defining a substantially open hollow interior and each including upper and lower vertebral engaging surfaces that each define an opening in communication with said hollow interior to facilitate fusion with the adjacent vertebrae; and
wherein said protrusion of said first interbody cage is engaged in said socket of said second interbody cage to interconnect said first and second interbody cages; and
wherein the interbody implant comprises a horseshoe-shaped or U-shaped implant assembly having two generally linear lateral portions extending substantially parallel to one another in an anterior-posterior direction and a central portion defining a generally semi-circular curvature extending between said generally linear lateral portions.

19. The implant of claim 18, further comprising bone graft material positioned within said hollow interior of said first and second interbody cages to further facilitate fusion with the adjacent vertebrae.

20. The implant of claim 18, wherein each of said first and second interbody cages includes opposite side surfaces and an opening passing therethrough between said opposite side surfaces.

21. The implant of claim 18, wherein said socket is defined by a plurality of elastic tongues that are engaged about said protrusion to maintain said first interbody cage in engagement with said second interbody cage.

22. The implant of claim 18, wherein said first and second interbody cages each have a height between said upper and lower surfaces that progressively tapers to generally match a lordotic angle between the adjacent vertebrae.

23. The implant of claim 18, wherein each of said first and second interbody cages includes a front face defining a hole for connection with an implantation tool.

24. The implant of claim 18, wherein each of said first and second interbody cages includes one of said lateral portions of said implant assembly and also includes an arc-shaped portion extending along approximately one-quarter of a circle, said arc-shaped portions of said interbody cages interconnected to one another by engagement of said protrusion in said socket to define said semi-circular curvature of said central portion of said implant assembly.

25. An interbody implant for implantation between adjacent vertebrae, comprising:
   a first interbody cage having a protrusion extending therefrom;
   a second interbody cage defining a socket;
   said first and second interbody cages each defining a substantially open hollow interior and each including upper and lower vertebral engaging surfaces that each define an opening in communication with a said hollow interior to facilitate fusion with the adjacent vertebrae; and
   wherein said protrusion of said first interbody cage is engaged in said socket of said second interbody cage to interconnect said first and second interbody cages; and
   wherein each of said first and second interbody cages includes a a lateral portion oriented in a posterior-anterior direction and an arc-shaped portion extending along approximately one-quarter of a circle, said arc-shaped portion of said first interbody cage connected to said arc-shaped portion of said second interbody cage by engagement of said protrusion of said first interbody cage in said socket of said second interbody cage; and
   wherein said first and second interbody cages are interconnected to define a U-shaped implant assembly.

* * * * *